(12) United States Patent
Gibson (10) Patent No.: US 7,406,352 B2
(45) Date of Patent: *Jul. 29, 2008

(54) LAMINATED ELECTRODE FOR A COCHLEAR IMPLANT

(75) Inventor: Peter Gibson, Randwick (AU)

(73) Assignee: Cochlear Limited, Lane Cove, New South Wales (AU)

( * ) Notice: Subject to any disclaimer, the term of this patent is extended or adjusted under 35 U.S.C. 154(b) by 468 days.

This patent is subject to a terminal disclaimer.

(21) Appl. No.: 10/473,379

(22) PCT Filed: Mar. 12, 2002

(86) PCT No.: PCT/AU02/00279

§ 371 (c)(1),
(2), (4) Date: Mar. 24, 2004

(87) PCT Pub. No.: WO02/078575

PCT Pub. Date: Oct. 10, 2002

(65) Prior Publication Data

US 2004/0172118 A1    Sep. 2, 2004

(30) Foreign Application Priority Data

Mar. 29, 2001 (AU) .................................. PR4080

(51) Int. Cl.
*A61N 1/05* (2006.01)
(52) U.S. Cl. .................... 607/137; 607/55; 607/56; 607/57
(58) Field of Classification Search ............. 607/55–57, 607/137
See application file for complete search history.

(56) References Cited

U.S. PATENT DOCUMENTS 4,357,497 A    11/1982    Hochmair et al.

(Continued)

FOREIGN PATENT DOCUMENTS

AU    WO 97/10784    * 4/1997    ................. 607/137

(Continued)

OTHER PUBLICATIONS

International Search Report of PCT/AU02/00279, dated Apr. 15, 2002.

(Continued)

*Primary Examiner*—Mark Bockelman
*Assistant Examiner*—Eric D Bertram
(74) *Attorney, Agent, or Firm*—Christie, Parker & Hale, LLP (57) ABSTRACT

An implantable cochlear implant electrode array (30) that can adopt a first, preferably straight, configuration selected to allow the array to be inserted into the cochlea and at least a second, preferably, spirally curved, configuration wherein the electrode array (30) is adapted to apply tissue stimulation. The electrode array (30) comprises an elongate carrier (31) having a proximal end (37), a distal end (34), and a plurality of electrodes supported by the carrier (31) at respective spaced locations thereon, the carrier (31) is formed, preferably moulded, to preferentially adopt the second configuration or another configuration different to said first configuration. The outer layer (33) is releasably connected to the elongate carrier (31) by an adhesive layer (32) and is formed so as to bias the carrier (31) into the first configuration when connected thereto. A method of forming the electrode array (30) is also disclosed.

23 Claims, 4 Drawing Sheets

U.S. PATENT DOCUMENTS

| | | | |
|---|---|---|---|
| 4,532,930 A | 8/1985 | Crosby et al. | |
| 4,686,765 A | 8/1987 | Byers et al. | |
| 4,819,647 A | 4/1989 | Byers et al. | |
| 5,037,497 A | 8/1991 | Stypullkowski | |
| 5,545,219 A | 8/1996 | Kuzma | |
| 5,578,084 A | 11/1996 | Kuzma et al. | |
| 5,645,585 A * | 7/1997 | Kuzma | 623/10 |
| 5,653,742 A | 8/1997 | Parker et al. | |
| 5,720,009 A | 2/1998 | Kirk et al. | |
| 5,999,859 A | 12/1999 | Jolly | |
| 6,038,484 A | 3/2000 | Kuzma | |
| 6,070,105 A | 5/2000 | Kuzma | |
| 6,078,841 A | 6/2000 | Kuzma | |
| 6,119,044 A | 9/2000 | Kuzma | |
| 6,125,302 A * | 9/2000 | Kuzma | 607/137 |
| 6,144,883 A | 11/2000 | Kuzma | |
| 6,195,586 B1 * | 2/2001 | Kuzma | 607/137 |
| 6,374,143 B1 | 4/2002 | Berrang et al. | |
| 6,397,110 B1 | 5/2002 | Kuzma | |
| 6,757,970 B1 | 7/2004 | Kuzma et al. | |
| 2003/0236562 A1 | 12/2003 | Kuzma | |
| 2004/0116995 A1 | 6/2004 | Dadd | |

FOREIGN PATENT DOCUMENTS

| | | |
|---|---|---|
| JP | 5-49701 | 3/1993 |
| JP | 10-234866 | 9/1998 |
| JP | 11-502441 | 3/1999 |
| JP | 11-502441 T | 3/1999 |
| WO | WO 93/06698 | 4/1993 |
| WO | WO 97/10784 | 3/1997 |

OTHER PUBLICATIONS

International Preliminary Examination Report of PCT/AU02/00279, dated Jun. 5, 2003.
Corresponding Australian Search Report, dated May 23, 2001.
Patent Abstracts of Japan, Publication No. 05-049701, dated Mar. 2, 1993, in the name of Hiroshi Nakajima et al.
International Search Report for PCT/AU01/01541, dated Dec. 11, 2001, in the name of Cochlear Limited et al.
Australian Search Report, dated Jan. 18, 2001, in the name of Cochlear Limited.
International Search Report for Australian Patent PR3646, dated May 23, 2001, in the name of Cochlear Limited.
Supplementary Partial European Search Report, dated Apr. 27, 2007, for EP 01998139.8, in the name of Cochlear Limited.

* cited by examiner

LAMINATED ELECTRODE FOR A COCHLEAR IMPLANT

CROSS-REFERENCE TO RELATED APPLICATION

This application is a National Phase Patent Application of International Application Number PCT/AU02/00279, filed on Mar. 12, 2002, which claims priority of Australian Patent Application Number PR 4080, filed on Mar. 29, 2001.

FIELD OF THE INVENTION

The present invention relates to an implantable device and, in particular, to an implantable cochlear electrode assembly. A method of manufacturing such a device is also described.

BACKGROUND OF THE INVENTION

Hearing loss, which may be due to many different causes, is generally of two types, conductive and sensorineural. Of these, conductive hearing loss occurs where the normal mechanical pathways for sound to reach the hair cells in the cochlea are impeded, for example, by damage to the ossicles. Conductive hearing loss may often be helped by use of conventional hearing aids, which amplify sound so that acoustic information does reach the cochlea and the hair cells.

In many people who are profoundly deaf, however, the reason for their deafness is sensorineural hearing loss. This type of hearing loss is due to the absence of, or destruction of, the hair cells in the cochlea which transduce acoustic signals into nerve impulses. These people are thus unable to derive suitable benefit from conventional hearing aid systems, no matter how loud the acoustic stimulus is made, because there is damage to or absence of the mechanism for nerve impulses to be generated from sound in the normal manner.

It is for this purpose that cochlear implant systems have been developed. Such systems bypass the hair cells in the cochlea and directly deliver electrical stimulation to the auditory nerve fibres, thereby allowing the brain to perceive a hearing sensation resembling the natural hearing sensation normally delivered to the auditory nerve. U.S. Pat. No. 4,532,930, the contents of which are incorporated herein by reference, provides a description of one type of traditional cochlear implant system.

Typically, cochlear implant systems have consisted of essentially two components, an external component commonly referred to as a processor unit and an internal implanted component commonly referred to as a receiver/stimulator unit. Traditionally, both of these components have cooperated together to provide the sound sensation to a user.

The external component has traditionally consisted of a microphone for detecting sounds, such as speech and environmental sounds, a speech processor that converts speech into a coded signal, a power source such as a battery, and an external transmitter coil.

The coded signal output by the speech processor is transmitted transcutaneously to the implanted receiver/stimulator unit situated within a recess of the temporal bone of the user. This transcutaneous transmission occurs via the external transmitter coil which is positioned to communicate with an implanted receiver coil provided with the receiver/stimulator unit. This communication serves two essential purposes, firstly to transcutaneously transmit the coded sound signal and secondly to provide power to the implanted receiver/stimulator unit. Conventionally, this link has been in the form of a radio frequency (RF) link, but other such links have been proposed and implemented with varying degrees of success.

The implanted receiver/stimulator unit traditionally includes a receiver coil that receives the coded signal and power from the external processor component, and a stimulator that processes the coded signal and outputs a stimulation signal to an intracochlea electrode assembly which applies the electrical stimulation directly to the auditory nerve producing a hearing sensation corresponding to the original detected sound.

Traditionally, at least the speech processor of the external componentry has been carried on the body of the user, such as in a pocket of the user's clothing, a belt pouch or in a harness, while the microphone has been mounted on a clip mounted behind the ear or on the lapel of the user.

More recently, due in the main to improvements in technology, the physical dimensions of the sound processor have been able to be reduced allowing for the external componentry to be housed in a small unit capable of being worn behind the ear of the user. This unit allows the microphone, power unit and the sound processor to be housed in a single unit capable of being discretely worn behind the ear, with the external transmitter coil still positioned on the side of the user's head to allow for the transmission of the coded sound signal from the sound processor and power to the implanted stimulator unit.

It is known in the art that the cochlea is tonotopically mapped. In other words, the cochlea can be partitioned into regions, with each region being responsive to signals in a particular frequency range. This property of the cochlea is exploited by providing the electrode assembly with an array of electrodes, each electrode being arranged and constructed to deliver a stimulating signal within a preselected frequency range to the appropriate cochlea region. The electrical currents and electric fields from each electrode stimulate the nerves disposed on the modiolus of the cochlea.

It has been found that in order for these electrodes to be effective, the magnitude of the currents flowing from these electrodes and the intensity of the corresponding electric fields, are a function of the distance between the electrodes and the modiolus. If this distance is relatively great, the threshold current magnitude must be larger than if the distance is relatively small. Moreover, the current from each electrode may flow in all directions, and the electrical fields corresponding to adjacent electrodes may overlap, thereby causing cross-electrode interference. In order to reduce the threshold stimulation amplitude and to eliminate cross-electrode interference, it is advisable to keep the distance between the electrode array and the modiolus as small as possible. This is best accomplished by providing the electrode array in a shape which generally follows the shape of the modiolus. Also, this way the delivery of the electrical stimulation to the auditory nerve is most effective as the electrode contacts are as close to the auditory nerves that are particularly responsive to selected pitches of sound waves.

In order to achieve this electrode array position close to the inside wall of the cochlea, the electrode assembly can be designed such that it assumes this position upon or immediately following insertion into the cochlea. This is a challenge as the assembly needs to be shaped such that it assumes a curved shape to conform with the shape of the modiolus and must also be shaped such that the insertion process causes minimal trauma to the sensitive structures of the cochlea. In this regard, it has been found to be desirable that the electrode assembly be generally straight during the insertion procedure.

Several procedures have been adopted to provide an electrode assembly that is relatively straight during initial insertion while adopting a curved configuration following insertion in the cochlea. In one case, a platinum wire stylet is used to hold a pre-curved electrode assembly in a generally straight configuration up until insertion. The platinum wire is inserted into lumen or channel located in the pre-curved electrode assembly with such lumen/channel allowing a passageway to accommodate the stylet. During or immediately following insertion, the platinum stylet is withdrawn allowing the assembly to return to its pre-curved configuration.

A number of methods of positioning the electrode assembly closer to the modiolus have also been developed. A number of these methods involve the use of space-filling positioners which are inserted in the cochlea and act to essentially fill the space inside the cochlea and behind the inserted electrode array, thereby forcing the electrode array into position close to the modiolus. Such methods are however very invasive and have a greater potential to cause damage to the existing sensitive structures of the cochlea. Also such techniques prevent the user from utilising any residual hearing that may be present and severely impact on the natural hydrodynamic behaviour of the cochlea.

The present invention is directed to an electrode assembly that can preferably be inserted more deeply into the cochlea whilst also preferably reducing the degree of trauma to the sensitive structures within the cochlea.

Any discussion of documents, acts, materials, devices, articles or the like which has been included in the present specification is solely for the purpose of providing a context for the present invention. It is not to be taken as an admission that any or all of these matters form part of the prior art base or were common general knowledge in the field relevant to the present invention as it existed in Australia before the priority date of each claim of this application.

SUMMARY OF THE INVENTION

Throughout this specification the word "comprise", or variations such as "comprises" or "comprising", will be understood to imply the inclusion of a stated element, integer or step, or group of elements, integers or steps, but not the exclusion of any other element, integer or step, or group of elements, integers or steps.

The present invention preferably provides a very thin electrode array that can be inserted close to the modiolus. The electrode array preferably has minimal impact on the hydrodynamic behaviour of the cochlea and allows the user to gain maximum benefit from any residual hearing that they may possess.

A relatively thin array also has the advantage of having a relatively light restoring force in its shape memory. This serves to minimise the potential force on the modiolus from the thin spiral electrode. By minimising the force on the modiolus, the electrode array can be preferably formed to have a tighter curvature than that of the modiolus, without fear that the force of the electrode on the modiolus will cause damage from long term implantation. It also has the advantage of providing a snug fit of the electrode against the modiolus.

According to a first aspect, the present invention is an implantable electrode array that can adopt a first configuration selected to allow the array to be inserted into an implantee's body and at least a second configuration wherein said electrode array is adapted to apply tissue stimulation, the array comprising:

an elongate carrier having a proximal end and a distal end, a plurality of electrodes supported by the carrier at respective spaced locations thereon in a region between the proximal end and the distal end, the carrier being formed to preferentially adopt the second configuration or another configuration different to said first configuration; and an outer layer releasably connected to the elongate carrier, the outer layer being formed so as to bias the carrier into the first configuration prior to insertion of the array into the implantee's body.

In a preferred embodiment, the implantable electrode array is a cochlear implant electrode array that is adapted for insertion into the cochlea of an implantee. Preferably, the array is adapted for insertion into the scala tympani of the cochlea of the implantee.

In a further embodiment, the elongate carrier has an inner surface designed to conform, following implantation, substantially with the inner wall of the cochlea.

In a still further embodiment, at least one of the electrodes has a surface that is at least adjacent the inner surface of the carrier. More preferably, each of the electrodes in the array have a surface that is adjacent the inner surface of the carrier. In a further embodiment, the surfaces of the electrodes are aligned with the inner surface of the carrier. In another embodiment, the surfaces of the electrodes stand proud of the inner surface of the carrier. It is also envisaged that the electrode surface could also be recessed into the inner surface of the carrier. In yet another embodiment, one or more electrodes may also be positioned on the outer surface of the carrier not facing the modiolus. Such electrodes could act as additional ground or reference electrodes.

In another embodiment, the outer layer can have a length such that it extends from the proximal end to the distal end of the carrier. In another embodiment, the outer layer may have a length longer than the distance between the proximal end and distal end of the carrier. It is also envisaged that the outer layer could have a length shorter than the distance between the proximal end and distal end of the carrier.

In yet another embodiment, a straightening stylet may also be incorporated in the outer layer or even in the adhesive layer to ensure that the outer layer or adhesive layer and hence the combined system maintains a relatively straight configuration during the insertion process. It is also envisaged that the outer layer could be reinforced with one or more metal or plastic reinforcing ribs to maintain the outer layer and hence the electrode array in a substantially straight configuration.

In another embodiment, the outer layer may be moulded with a preferential curvature opposite to the preferential curvature of the carrier rather than being merely straight. In such a configuration, following the adhesion of the two layers together, the inherent curvature of each of the two members can act to balance each other out resulting in a substantially straight configuration.

While the array could incorporate additional layers than that defined above, for simplicity, the invention will mainly be described below as consisting of the carrier and the releasably connected outer layer.

In one embodiment, the outer layer can be formed from a material different to that of the carrier. In another embodiment, the carrier and outer layer can be formed from the same material. In this latter case, the carrier and outer layer can have different mechanical properties despite being formed of the same material.

In one embodiment, the carrier and the outer layer can be formed from a biocompatible elastomeric material. In one embodiment, the elastomeric material can be a silicone rubber. In another embodiment, the elongate carrier and/or outer layer can be formed from a biocompatible polyurethane. Still further, the outer layer may be formed from a polyethylene terephthalate (PET), polytetrafluoroethylene (PTFE) or a biocompatible metal, such as platinum, iridium, stainless steel, or a shape memory metal (eg. Nitinol™), or a shape memory polymer (SMP).

In a further embodiment, the thickness of the carrier between its inner surface and outer surface can be substantially constant for at least a majority of its length from the proximal end to the distal end. In another embodiment, the thickness of the carrier can change, such as decrease, from the proximal end to the distal end. In a preferred embodiment, the carrier can be relatively more resiliently flexible in a longitudinal plane and relatively less resiliently flexible in a lateral plane. In one embodiment, the carrier can have an oval-shaped cross-section and is preferably relatively more flexible in the direction of curvature of the cochlea and relatively stiffer in other planes.

In a further embodiment, the carrier can have a thickness of between about 0.20 mm and 0.30 mm, more preferably 0.25 mm.

In a further embodiment, the thickness of the outer layer can be constant for at least a majority of its length. In a still further embodiment, the thickness of the outer layer can change, such as decrease, from its proximal end to its distal end.

In a still further embodiment, the thickness of the outer layer can be greater than the carrier. In one embodiment, the outer layer has a thickness between about 0.3 mm and 0.55 mm.

In a preferred embodiment, the carrier is preferably relatively resiliently flexible such that, despite its propensity to normally adopt a spirally curved configuration, it adopts the substantially straight or straight configuration of the releasably connected outer layer prior to implantation.

Preferably, the curved configuration of the array following completion of implantation is such that the carrier can fit inside the cochlea of the implantee with said adjacent surfaces of the electrodes being proximal to the modiolus of the cochlea.

The outer surface of the outer layer of the array is preferably smooth to prevent any damage to the cochlea as the array is inserted into the cochlea.

The outer layer is preferably releasably connected to the carrier by an intermediate layer of a bioresorbable adhesive that softens or dissolves on exposure to a fluid. The adhesive layer preferably softens or dissolves on exposure to a saline solution or a body fluid of the implantee, such as cochlear fluid. As the adhesive layer softens, it preferably becomes lubricious allowing the carrier to begin to adopt its normal preferential curved configuration. It is also envisaged that the adhesive layer could be made from an adhesive impregnated in a fibre (eg. in much the same way as fibreglass). The fibre could be a type of plastics material and would make the adhesive layer stiffer, which would ultimately assist in keeping the array straight. It is also possible that the fibre may assist in the transportation of fluid into the adhesive layer to promote rapid dissolution of the adhesive layer.

It will be appreciated that due to the constraints imposed by the geometry of the cochlea and/or the presence of the carrier within the cochlea, the carrier may not adopt a curved configuration identical to that that can be adopted by the carrier prior to it being adhered to the outer layer. In one embodiment, the carrier, prior to being adhered to the outer layer, preferably subtends an angle at least greater than about 450°. Following implantation, the carrier preferably subtends an angle of at least about 360°.

In a further embodiment, the bioresorbable material of the adhesive layer is selected from the group consisting of polyacrylic acid (PAA), polyvinyl alcohol (PVA), polylactic acid (PLA) and polyglycolic acid (PGA). It is envisaged that other similar materials could also be used.

In one embodiment, at least a portion of the carrier may be releasably attached to at least a portion of the outer layer by an attachment means other than said adhesive layer. For example, the distal end of the carrier may be releasably attached to the distal end of the outer layer. More than one such attachment means may exist between the carrier and the outer layer. The attachment means may be provided by a non-bioresorbable adhesive. In another embodiment, the attachment means may comprise an integral connection between the carrier and outer layer. Still further, the attachment means may be a disengageable attachment means.

In a preferred embodiment, the electrode array can include electrically conducting connections, such as wires, connected to the electrodes and extending to at least said proximal end. In one embodiment, the connections can be connected to each of said electrodes. In another embodiment, at least two connections can be connected to each of said electrodes.

Each electrode can comprise a contact element. The carrier, when straightened, can have a longitudinal axis with each contact element arranged orthogonally to the longitudinal axis. The contact elements can be formed from a biocompatible material. The biocompatible material of the contact element can be platinum. The wires are preferably connected to the contact elements by welding.

Once implanted, the electrodes of the carrier member preferably receive stimulation signals from a stimulator means. The stimulator means is preferably electrically connected to the elongate carrier member by way of an electrical lead. The lead can include the one or more wires extending from each electrode of the array mounted on the elongate member.

In one embodiment, the lead can extend from the elongate member to the stimulator means or at least the housing thereof. In one embodiment, the lead is continuous with no electrical connectors, at least external the housing of the stimulator means, required to connect the wires extending from the electrodes to the stimulator means. One advantage of this arrangement is that there is no requirement for the surgeon implanting the device to make the necessary electrical connection between the wires extending from the electrodes and the stimulator means.

The stimulator means is preferably positioned within a housing that is implantable within the implantee. The housing for the stimulator means is preferably implantable within a recess in the bone behind the ear posterior to the mastoid.

When implanted, the housing preferably contains, in addition to the stimulator means, a receiver means. The receiver means is preferably adapted to receive signals from a controller means. The controller means is, in use, preferably mounted external to the body of the implantee such that the signals are transmitted transcutaneously through the skin of the implantee.

Signals can preferably travel from the controller means to the receiver means and vice versa. The receiver means can include a receiver coil adapted to receive radio frequency (RF) signals from a corresponding transmitter coil worn externally of the body. The radio frequency signals can comprise frequency modulated (FM) signals. While described as a receiver coil, the receiver coil can preferably transmit signals to the transmitter coil which receives the signals.

The transmitter coil is preferably held in position adjacent the implanted location of the receiver coil by way of respective attractive magnets mounted centrally in, or at some other position relative to, the coils.

The external controller can comprise a speech processor adapted to receive signals output by a microphone. During use, the microphone is preferably worn on the pinna of the implantee, however, other suitable locations can be envisaged, such as a lapel of the implantee's clothing. The speech processor encodes the sound detected by the microphone into a sequence of electrical stimuli following given algorithms, such as algorithms already developed for cochlear implant systems. The encoded sequence is transferred to the implanted receiver/stimulator means using the transmitter and receiver coils. The implanted receiver/stimulator means demodulates the FM signals and allocates the electrical pulses to the appropriate attached electrode by an algorithm which is consistent with the chosen speech coding strategy.

The external controller further comprises a power supply. The power supply can comprise one or more rechargeable batteries. The transmitter and receiver coils are used to provide power via transcutaneous induction to the implanted receiver/stimulator means and the electrode array.

While the implant system can rely on external componentry, in another embodiment, the controller means, including the microphone, speech processor and power supply can also be implantable. In this embodiment, the controller means can be contained within a hermetically sealed housing or the housing used for the stimulator means.

In yet a further embodiment, a longitudinal lumen can extend through the carrier and/or the outer layer for at least a portion of their respective lengths. The lumen can act as a substance delivery means for delivering a bioactive substance to the implant site following implantation.

The lumen can act as a reservoir for the bioactive substance. In one embodiment, the bio-active substance in the reservoir can leach from the lumen into the surrounding material of the carrier or outer layer and eventually migrate out of the array to the desired site of action for the bio-active substance. In another embodiment, the carrier and/or outer layer can have one or more substance egress means whereby the bioactive substance can move out of the lumen and through the carrier and/or outer layer to a position that is preferably close to the desired site of action for the bio-active substance.

Where the bioactive substance is carried in or comprises a fluid, each substance egress means preferably comprises a fluid egress means.

Each fluid egress means preferably has a valve means that allows fluid to exit the lumen but prevents, or at least substantially prevents, fluid flow from external the elongate member back into the lumen.

In a further embodiment, the proximal opening of the lumen can be in fluid communication with an additional reservoir for the bioactive substance that is external to the array. A pumping means, such as an osmotic pump, can transfer the bioactive substance from the additional reservoir into the lumen for subsequent delivery to the appropriate site of action.

It is also envisaged that the bioactive substance can be captured in the form of a solid pellet. An example of how this may occur is by impregnating the bioactive substance in a ceramic or a polymer pellet that has a predetermined rate of release of the bioactive substance. This solid pellet can then be stored in the lumen reservoir or in an external reservoir connectable to the lumen.

In one embodiment, the bioactive substance can comprise a steroid. In another embodiment, the bioactive substance can perform a function of reducing the resting neuron potential of neurons within the cochlea. The use of such substances can result in less energy being required to excite the neurons and cause stimulation. In yet another embodiment, the bioactive substance can comprise a nerve growth factor and mimetics to enhance the survival and growth of the nerve cells in the cochlea to improve the performance of the cochlear implant.

In a still further embodiment, at least a portion of the surface of the carrier can have a coating of lubricious material. In a further embodiment, a substantial portion of the surface can have a coating of the lubricious material.

The lubricious material preferably becomes lubricious on being brought into contact with a fluid, such as a saline solution. Still further, the coating preferably becomes lubricious on being brought into contact with a body fluid, such as cochlear fluid.

In one embodiment, the lubricious material is selected from the group consisting of polyacrylic acid (PM), polyvinyl alcohol (PVA), polylactic acid (PLA) and polyglycolic acid (PGA). It is envisaged that other similar materials could also be used. It is envisaged that the lubricious material can also be impregnated with the bioactive substance allowing the coating to perform a dual role. The rate of delivery of the bioactive substance can be programmed by design of the coating structure.

In a still further embodiment, the array can be enveloped by a stiffening sheath which is made of a material that is relatively stiffer than the resiliently flexible material of the carrier. The stiffening sheath can be adapted to assist in biasing the array into at least a substantially straight configuration prior to implantation. In one embodiment, the stiffening sheath can be overlaid by the coating of lubricious material.

The stiffening sheath, if present, can be formed of a bioresorbable material which dissolves or softens on exposure to a fluid. The stiffening sheath can dissolve or soften on exposure to a saline solution or a body fluid of the implantee, such as cochlear fluid, and in doing so also release one or more bio-active substances impregnated therein.

In a further embodiment, the bioresorbable material of the stiffening sheath is selected from the group consisting of polyacrylic acid (PM), polyvinyl alcohol (PVA), polylactic acid (PLA) and polyglycolic acid (PGA). It is also envisaged that other suitable materials could also be used. It is envisaged that the bioresorbable element of the stiffening sheath can also be impregnated with one or more bioactive substances allowing the stiffening sheath to perform a dual role. The rate of delivery of the bioactive substance can be programmed by design of the sheath structure.

The array can still further include an additional layer surrounding the stiffening sheath. The additional layer can have a first rate of fluid ingress therethrough and have at least one fluid ingress means formed therein, the rate of fluid ingress through the fluid ingress means being greater than the first rate of fluid ingress through the additional layer. In this embodiment, the coating of lubricious material can be coated on the outside of the additional layer.

The fluid ingress means can comprise one or more openings in the additional layer. The openings can be closable. The openings can comprise slits in the additional layer. The slits can be formed to allow substantially the same or the same rate of ingress of fluid through the additional layer. In another embodiment, at least one slit can allow a different rate of progress of fluid through the additional layer compared to the other slits.

The present invention provides a surgeon with a cochlear implant electrode array that can potentially be inserted to a greater depth than hitherto known electrode arrays whilst maintaining close proximity between the surfaces of the electrodes and the modiolus. In particular, by removing the need to withdraw a stylet or other stiffening member from the array during implantation, the surgeon is provided with a more straightforward means of achieving successful implantation of the array. Still further, the device can be used to deliver a relatively thin electrode array to within the cochlea. The placement of a relatively thin electrode array should help to preserve the hydrodynamic behaviour of the cochlea, thus also giving the maximum possibility of preserving residual hearing.

According to a further aspect, the present invention is a method of manufacturing an implantable electrode array that can adopt a first configuration selected to allow the array to be inserted into an implantee's body and at least a second configuration wherein said electrode array is adapted to apply tissue stimulation, the method comprising the steps of:

(i) moulding an elongate carrier in a curved configuration in a first mould from a resiliently flexible material about an array of electrodes such that at least one of the electrodes has a surface that is at least adjacent an inner surface of the carrier;

(ii) separately moulding at least an outer layer of the array in a second mould from a resiliently flexible material, the outer layer being moulded such that in combination with the elongate carrier the electrode array is in a substantially straight or straight configuration;

(iii) removing the elongate carrier and the outer layer from the respective first and second moulds; and (iv) straightening the carrier member and removably adhering it to the outer layer using a bioresorbable adhesive.

The carrier can be formed about an array of electrodes such that at least one of the electrodes has a surface that is at least adjacent an inner surface of the carrier.

In a preferred embodiment, the electrodes can comprise a plurality of contact elements. The electrodes can be formed from a biocompatible material, such as platinum. The electrode array is preferably formed by positioning a series of platinum contact members on or about a longitudinal support that is preferably removable once the carrier has been moulded about the electrodes. The support can comprise a wire that is coated with a low-friction material, such as polytetrafluroethylene (PTFE).

Once positioned about the PTFE-coated wire, a series of electrically conducting wires can be welded to each of the electrodes. Each electrode preferably has at least one, and more preferably two, electrically conducting wires welded thereto. Alternatively, the electrodes could be fabricated by thin film photo-lithographic techniques as described in the Applicant's U.S. Pat. No. 5,720,009 the contents of which are incorporated herein by reference.

Once the electrodes are positioned about the PTFE-coated wire, the electrodes are placed in the first mould to allow moulding of the carrier.

In a preferred embodiment, the electrode array is adapted for insertion into the cochlea. As such, it is preferred that the electrode array, once implanted, will adopt a configuration that substantially matches the spiral configuration of the cochlea. To assist the electrode array in forming a spiral configuration following implantation, the carrier is moulded in a spirally curved mould. The first mould preferably forms a carrier that subtends an arc of around 4500 once formed. The first mould is preferably specifically adapted to form a carrier having a spiral shape that subtends an arc greater than that will be subtended by the array following completion of the implantation procedure. This is achieved by designing the mould so that the radius of each turn is reduced over the length of the mould, so that a tight curvature of the outer layer is achieved.

The second mould used to mould the outer layer is preferably substantially straight or straight such that the outer layer, following its manufacture and removal from the second mould, is substantially straight or straight, respectively.

The carrier is preferably formed from an elastomeric silicone material and remains in the first mould at least until completion of curing. The cured carrier may be straightened by and held straight in a straightening jig following its removal from the first mould.

The outer layer is also preferably formed from an elastomeric silicone material. The outer layer can be formed from the same material as the carrier or a different material. A straightening stylet may also be incorporated in the outer layer or even in the adhesive layer to ensure that the combined array maintains a relatively straight configuration during the insertion process. It is also envisaged that the outer layer could be reinforced with one or more metal or plastic reinforcing ribs to maintain the system in a substantially straight configuration.

In another embodiment, the outer layer may be moulded with a preferential curvature opposite to the preferential curvature of the carrier rather than being merely straight. In such a configuration, following the adhesion of the two layers together, the inherent curvature of the two members acts to negate each other resulting in a substantially straight configuration.

Once the outer layer is cured, it can be removed from the second mould. Following removal, the outer layer can then be adhered to the top of the cured carrier that is held in the straightening jig.

Once the outer layer is adhered to the carrier, the array formed by this process can be removed from the jig. The adhesive used to bond the carrier and outer layer can also help to retain the array in a straight or substantially straight configuration despite the propensity of the carrier to want to return to its moulded spiral shape.

According to a third aspect, the present invention is a method of inserting an implantable electrode array in a cochlea of an implantee comprising the steps of:

(i) performing a cochleostomy;

(ii) inserting the electrode array of claim 6 through the cochleostomy; and (iii) closing the cochleostomy.

In step (ii) of the method, the adhesive layer bonding the outer layer and carrier preferably gradually dissolves thereby allowing the carrier to move towards its second configuration.

During insertion into the cochlea, the electrode array would preferably conform to the outer wall, or if a malleable stylet is incorporated into the structure of the array, the array would conform to the shape of the cochlea upon insertion. The surgeon would cease insertion once the electrode array has been inserted to an appropriate depth, which may be indicated by a depth marker on the array. As the electrode array is exposed to cochlear fluid, the adhesive bonding the outer layer and carrier would begin to gradually dissolve. The rate of dissolution would be dependent on factors such as the degree of exposure of the adhesive layer to the cochlear fluid. Alternatively, or in addition, the surgeon could introduce a sterile saline type solution to the array following insertion to aid in the dissolution process.

As the adhesive softens and becomes more lubricious, the carrier gradually begins to move towards it natural curved configuration. As the carrier curves, it separates from the outer layer.

Following insertion and at dissolution of the adhesive layer, the outer layer can be withdrawn from the cochlea. This has the advantage of leaving only the relatively thin carrier positioned in the scala tympani.

BRIEF DESCRIPTION OF THE DRAWINGS

By way of example only, a preferred embodiment of the invention is now described with reference to the accompanying drawings, in which.

PREFERRED MODE OF CARRYING OUT THE INVENTION

Figure 1:
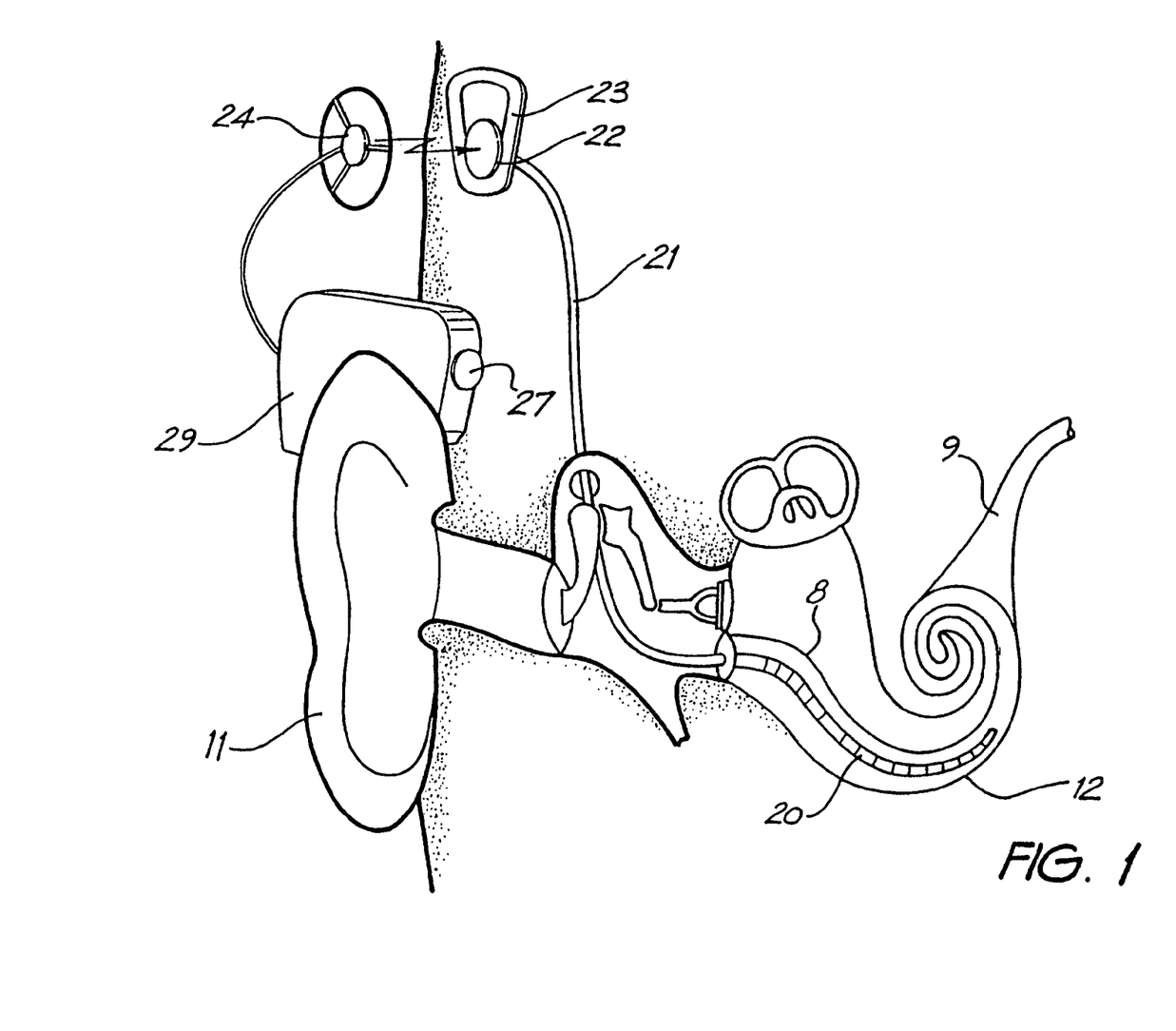
FIG. 1 is a pictorial representation of a prior art cochlear implant system.

Before describing the features of the present invention, it is appropriate to briefly describe the construction of one type of known cochlear implant system with reference to FIG. 1.

Known cochlear implants typically consist of two main components, an external component including a speech processor 29, and an internal component including an implanted receiver and stimulator unit 22. The external component includes a microphone 27. The speech processor 29 is, in this illustration, constructed and arranged so that it can fit behind the outer ear 11. Alternative versions may be worn on the body. Attached to the speech processor 29 is a transmitter coil 24 that transmits electrical signals to the implanted unit 22 via a radio frequency (RF) link.

The implanted component includes a receiver coil 23 for receiving power and data from the transmitter coil 24. A cable 21 extends from the implanted receiver and stimulator unit 22 to the cochlea 12 and terminates in an electrode array 20. The signals thus received are applied by the array 20 to the basilar membrane 8 and the nerve cells within the cochlea 12 thereby stimulating the auditory nerve 9. The operation of such a device is described, for example, in U.S. Pat. No. 4,532,930.

As depicted diagrammatically in FIG. 1, the cochlear implant electrode array 20 has traditionally been inserted into the initial portion of the scala tympani of the cochlea 12 up to about a full turn within the cochlea. The electrode array according to the present invention is adapted to be inserted more deeply into the cochlea 12 than has historically been the case.

One embodiment of a cochlear implant electrode array, according to the present invention, is depicted generally as 30 in the remaining drawings.

Figure 2:
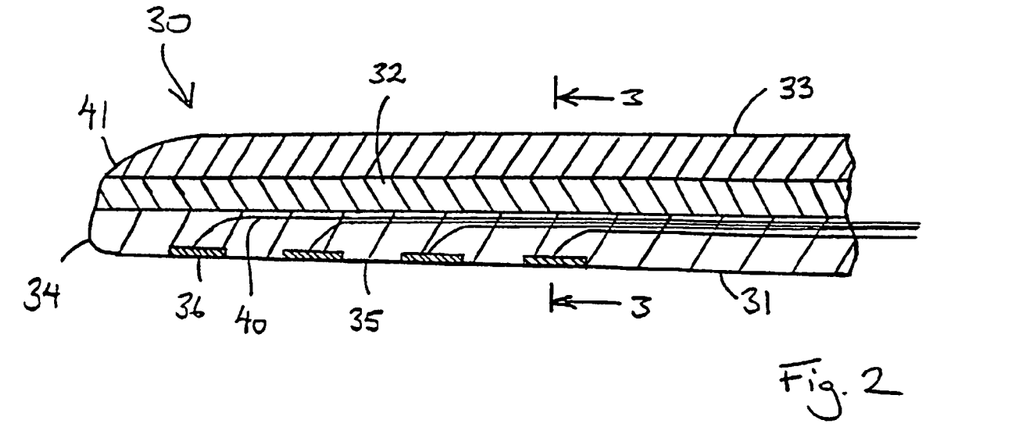
FIG. 2 is a simplified longitudinal sectional view of a cochlear electrode array according to the present invention in its pre-insertion state.
Figure 3:
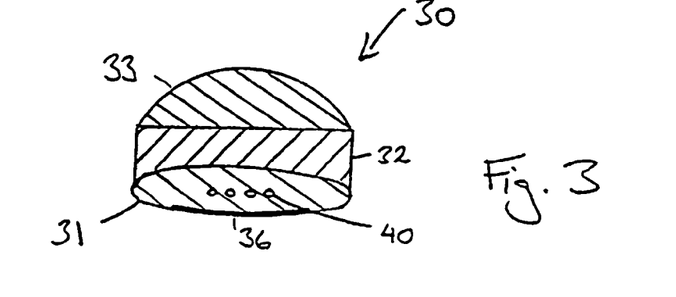
FIG. 3 is a sectional view taken along line 3-3 of FIG. 2.

The array 30 comprises an elongate electrode carrier member 31 of substantially oval cross-section, an intermediate adhesive layer 32, and an outer layer 33. The depicted carrier member 31 and outer layer 33 are each moulded from a suitable biocompatible resiliently flexible silicone. In the depicted embodiments, each layer 31,33 is formed from the same elastomeric silicone material. It will be understood by a person skilled in the art that the layers 31,33 could be formed from different materials to one another should a particular characteristic of the material be desired. Further, layer 33 could also include one or more reinforcing/stiffening ribs of a suitable material such as metal or plastic. In addition to or instead of the ribs, the outer layer 33 can have a lumen extending at least partially therethrough that is adapted to receive a metal or plastic straightening stylet. Such a stylet can be removable from the lumen of the outer layer 33 on insertion of the electrode array 30 into the cochlea of the implantee.

Following its manufacture, the array 30 is maintained in a substantially straight or straight configuration ready for insertion in the scala tympani of a human cochlea 12.

While the depicted array 30 normally adopts a substantially straight or straight configuration, following manufacture, it will be appreciated that the array 30 could be manufactured to adopt another configuration following manufacture.

The carrier member 31 has a first distal end 34 that is firstly inserted into the cochlea 12 upon insertion of the array 30. The carrier member also has an inner surface 35 adapted to be positioned at least close to the surface of the modiolus of the cochlea 12 following insertion of the array 30. Disposed within the carrier member 31 are a plurality of electrodes 36. It will be appreciated that the electrodes 36 depicted in the drawings are not necessarily drawn to scale. Further, more or less electrodes 36 than that depicted in the drawings could be utilised in the carrier member 31. Each electrode 36 comprises a platinum contact surface having an outer surface at least adjacent, and preferably substantially aligned with, the inner surface 35 of the carrier member 31. Each electrode 36 could also have a surface coating of some other metal such as Iridium or Rhodium and they could also-be made from a variety or combination of metals. At least one electrically conducting wire 40 extends from each of the electrodes 36 through the elongate member 31 to at least the proximal end 37 of the carrier member 31. The wires 40 extend back to an implanted receiver/stimulator unit, such as unit 22 depicted in FIG. 1.

The depicted adhesive layer 32 is formed from a bioresorbable material that softens or dissolves on exposure to cochlear fluid. As the adhesive layer 32 dissipates, it preferably becomes lubricious allowing the outer layer 33 to begin to separate from the carrier 31 and so allow the carrier to begin to adopt its normal preferentially curved configuration. It will, however, be appreciated that due to the constraints imposed by the geometry of the cochlea 12, the carrier 31 may not adopt a curved configuration identical to that that can be adopted by the carrier 31 prior to it being adhered to the straight outer layer 33.

In one embodiment, the carrier 31, prior to being adhered to the outer layer 33, subtends an angle at least greater than about 450°. Following implantation, the carrier 31 preferably subtends an angle of at least about 360°.

In the depicted embodiment, the bioresorbable material of the adhesive layer 32 is selected from the group consisting of polyacrylic acid (PAA), polyvinyl alcohol (PVA), polylactic acid (PLA) and polyglycolic acid (PGA). It is envisaged that other similar materials could also be used.

Figure 8:
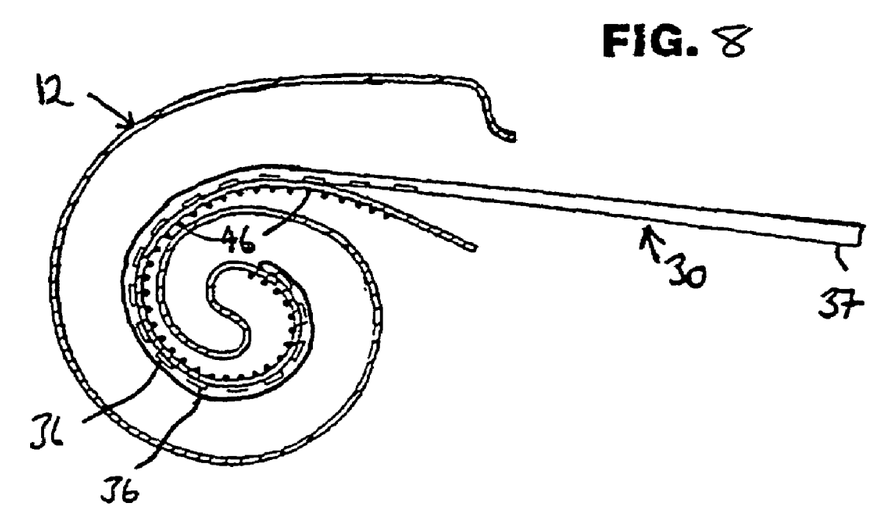

In the depicted embodiment, both the carrier 31 and the outer layer 33 are attached only by the adhesive layer 32. In this embodiment the outer layer 33 becomes fully disengaged from the carrier 31 allowing the outer layer 33 to be completely removed from the cochlea leaving only the thin carrier 31 positioned proximal the modiolus (as depicted in FIG. 8). In another embodiment, it will be appreciated that the distal end 34 of the carrier 31 may be attached to the distal end 41 of the outer layer by a non-bioresorbable adhesive. A similar attachment could also be provided between the proximal end 43 of the outer layer 33 and the carrier 31. It could be possible to have more than two such attachments between the carrier 31 and the outer layer 33. In such an embodiment, the outer layer would lengthen allowing the carrier to assume its position proximal to the modiolus. This could be done in a number of ways such as constructing the outer layer with a hydrogel type of material whereby upon exposure to fluid the outer layer would swell in a lengthwise mode. The outer layer could also achieve this by being constructed in a concertina-type arrangement and assembled in its compact form through use of a bioresorbable adhesive. In this arrangement, upon exposure to fluid, the outer layer would be permitted to expand hence allowing the carrier to assume its position proximal to the modiolus.

Prior to implantation, the outer layer 33 has a sufficient stiffness to retain the silicone elongate carrier member 31 in a straight configuration. As previously stated, it is also considered permissible that the outer layer could itself be pre-curved in an opposite manner to the pre-curve of the carrier so that together the array configuration would be naturally balanced straight. The bioresorbable material of the adhesive layer 32 can also be used to assist in retaining the straight configuration of the array 30.

Figure 4:
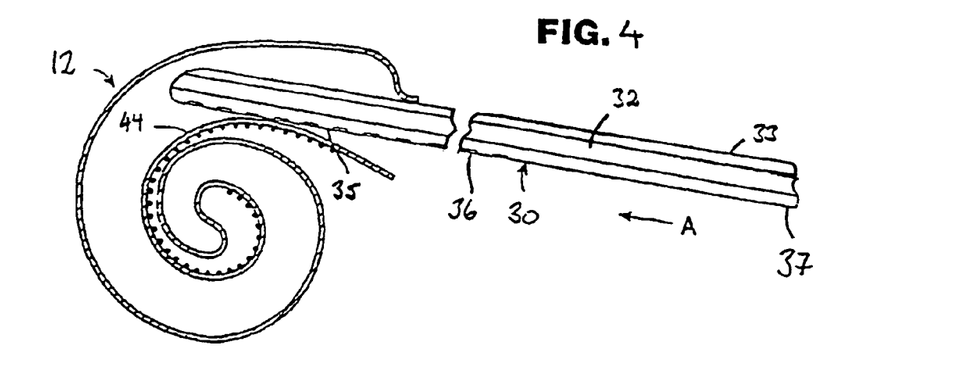
FIGS. 4, 5, 6 and 8 are simplified schematic illustrations of the initial, intermediate and final stages of the insertion of a cochlear electrode array according to the present invention into the cochlea of a human being.

The array 30 is typically delivered to a surgeon in a sterile package. Upon removal from the package, the array 30 is inserted into the scala tympani of the cochlea 12 as is depicted in FIG. 4, with the inner surface 35 of the carrier 31 directed towards the inner wall 44 of the cochlea 12. The array 30 is advanced into the cochlea by the surgeon pushing the array in direction of arrow A.

Figure 5:
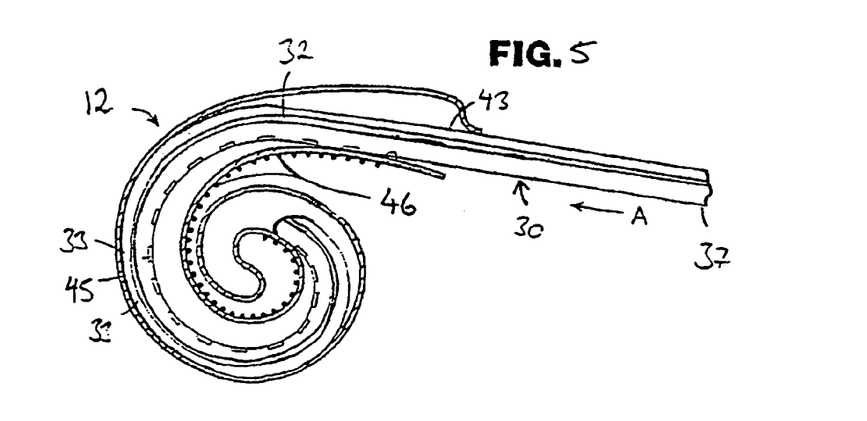

As the pushing continues, the array 30 enters the spirally curved section of the cochlea 12, with the outer surface of the outer layer 33 gliding gently along the radially outer wall 45 of the cochlea 12 (FIG. 5). As insertion continues and dissolution of the adhesive layer 32 continues, the carrier 31 begins to become detached from the outer layer 33 and the natural preferential curvature of the carrier 31 serves to move the carrier member 31 towards the inner wall 44 of the cochlea 12, with the result that the electrodes 36 facing the modiolus within the cochlea 12 are positioned as close as possible to the spiral ganglia 46 thereof (see FIG. 6).

The design of the cochlear implant electrode array 30 allows the elongate carrier member 31 to be inserted, in a typical case, more deeply into the scala tympani of the cochlea 12 than would be the case for hitherto traditionally used perimodular arrays, such as array 20 depicted in FIG. 1.

Figure 6:
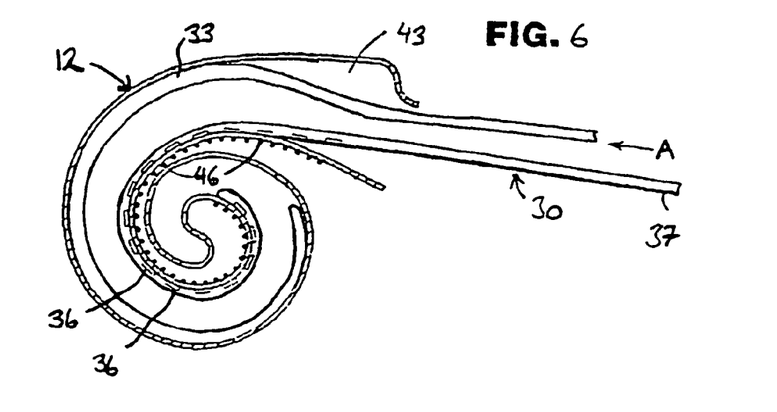

Following detachment of the carrier 31 from the outer layer 33 as is shown in FIG. 6, the outer layer 33 is withdrawn from the cochlea 12 leaving in place a thin electrode array proximal to the modiolus (FIG. 8).

To form the depicted electrode array 30, a plurality of platinum contact members, which become the electrodes 36, are mounted on a PTFE-coated wire. Each electrode 36 could also have a surface coating of some other metal such as Iridium or Rhodium and they could also be made from a variety or combination of such suitable metals. Each contact member 36 has one, or possibly two, conductive wires welded thereto to allow electrical connection from the implanted receiver/stimulator unit 22 to the contact members 36.

Figure 7:
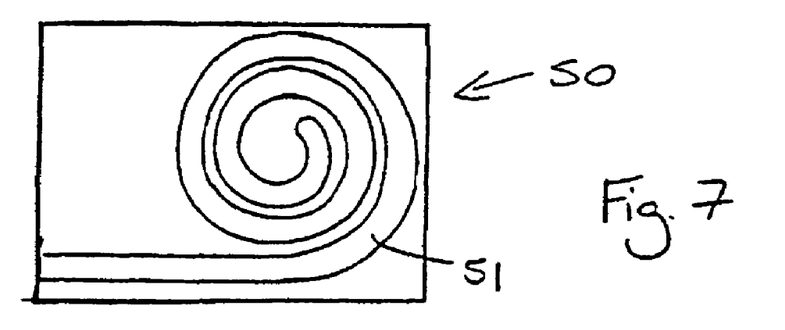
FIG. 7 is a plan view of a first mould according to the present invention for forming a carrier as defined herein.

Once formed, the electrode assembly is placed in a first spirally curved mould (such as the spiral-shaped channel 51 of second mould 50 depicted in FIG. 7), with the outer surfaces of the contact members 36 abutting the inner surface thereof. Once correctly positioned in the first mould 50, a silicone is poured or injected into the first mould 50 around the PTFE-coated wire and allowed to cure.

Meanwhile, the outer layer is formed in a second straight mould or is moulded in a mould so as to have a preferential curvature that is in a direction opposite to that of the carrier. Once cured, the formed elastomeric outer layer 33 can be removed from the second mould. The outer layer 33, on removal from the second mould, naturally adopts the straight configuration of the second mould.

Once removed from the first mould 50, the carrier 31 is straightened in a straightening jig. The straightening jig can comprise two grips that grip the respective ends of the carrier 31 and tension the carrier 31 to ensure it is at least substantially straight. The straight outer layer 33 is then adhered, using adhesive layer 32, to the carrier member 31.

Once the outer layer 33 has adhered to the carrier member 31, the array 30, the PTFE-coated wire can be removed from the member 31. The removal of the PTFE-coated wire leaves a longitudinal lumen in the carrier 31 (not depicted).

The use of the process as defined herein results in the formation of a straight electrode array 30 that will begin to adopt a curved configuration following implantation.

While the preferred embodiment of the invention has been described in conjunction with a cochlear implant, it is to be understood that the present invention has wider application to other implantable electrodes, such as electrodes used with pacemakers.

It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive.

The invention claimed is:

1. An implantable electrode array with an elongate carrier, that can adopt a first substantially straight configuration selected to allow the array to be inserted into an implantee's ear and a preferential second spirally curved configuration wherein said electrode array is adapted to apply tissue stimulation, the array comprising:

a proximal end; a distal end; a plurality of electrodes supported by the elongate carrier at respective spaced locations thereon in a region between the proximal end and the distal end; and a non-bioresorbable outer layer having a length, which biases the elongate carrier into said first substantially straight configuration, the outer layer being removably adhered to the elongate carrier along a majority of the length of the outer layer until full insertion of the array into the implantee's ear, and removable after full insertion to allow the elongate carrier to adopt the preferential second spirally curved configuration.

2. An implantable electrode array of claim 1 wherein the implantable electrode array is a cochlear implant electrode array insertable into the cochlea of an implantee.

3. An implantable electrode array of claim 2 wherein the elongate carrier has an inner surface that is substantially conformable, following insertion, with an inner wall of the cochlea.

4. An implantable electrode array of claim 3 wherein each of the electrodes have a surface that is at least adjacent the inner surface of the carrier.

5. An implantable electrode array of claim 1 wherein the outer layer has a length that extends from the proximal end to the distal end of the carrier.

6. An implantable electrode array of claim 5 wherein a straightening stylet extends through the outer layer to at least substantially straighten the outer layer and hence the electrode array into the first substantially straight configuration.

7. An implantable electrode array of claim 2 wherein the outer layer is reinforced with one or more reinforcing ribs to maintain the outer layer and hence the electrode array in the first substantially straight configuration.

8. An implantable electrode array of claim 2 wherein the outer layer is moulded with a preferential curvature opposite to the preferential curvature of the carrier thereby resulting in the electrode array having the first substantially straight configuration.

9. An implantable electrode array of claim 2 wherein the carrier and the outer layer are each formed from a biocompatible elastomeric material.

10. An implantable electrode array of claim 2 wherein the outer layer is removably adhered to the carrier by a layer of bioresorbable adhesive.

11. An implantable electrode array of claim 10 wherein the adhesive layer is formed from a bioresorbable material that softens or dissolves on exposure to a body fluid of the implantee.

12. An implantable electrode array of claim 11 wherein, following insertion, the carrier subtends an angle of at least about 360°.

13. An implantable electrode array of claim 11 wherein the bioresorbable material of the adhesive layer is selected from the group consisting of polyacrylic acid (PAA), polyvinyl alcohol (PVA), polylactic acid (PLA), and polyglycolic acid (PGA).

14. A method of inserting an implantable electrode array in a cochlea of an implantee comprising the steps of:
(i) performing a cochleostomy;
(ii) fully inserting the electrode array of claim 2 through the cochleostomy;
(iii) removing the non-bioresorbable outer layer from the elongate carrier after full insertion; and
(iv) closing the cochleostomy.

15. A method of inserting an implantable electrode array in a cochlea of an implantee of claim 14 wherein during step (ii) the adhesive layer bonding the outer layer and carrier gradually dissolves thereby allowing the carrier to move towards its second configuration.

16. A method of inserting an implantable electrode array in a cochlea of an implantee of claim 14 wherein following insertion of the electrode array, and at least partial dissolution of the adhesive layer, the outer layer is withdrawn from the cochlea.

17. A method of forming an implantable electrode array that can adopt a first substantially straight configuration selected to allow the array to be inserted into an implantee's body and a preferential second spirally curved configuration wherein said electrode array is adapted to apply tissue stimulation, the method comprising the steps of:
moulding an elongate carrier in a curved configuration in a first mould from a resiliently flexible material about an array of electrodes such that at least one of the electrodes has a surface that is at least adjacent an inner surface of the carrier;
separately moulding a non-bioresorbable outer layer of the array in a second mould from a resiliently flexible material, the outer layer being moulded in a substantially straight or straight configuration;
removing the elongate carrier and the outer layer from the respective first and second moulds; and
straightening the carrier member and removably adhering it to the outer layer along a majority of the length of the outer layer using a bioresorbable adhesive.

18. A method of forming an implantable electrode array of claim 17 wherein the electrode array is insertable into the cochlea of an implantee.

19. A method of forming an implantable electrode array of claim 17 wherein the first mould used to mould the carrier is spiral-shaped such that the carrier, following its manufacture and removal from the first mould, subtends an arc of about 450° or greater.

20. A method of forming an implantable electrode array of claim 17 wherein the second mould used to mould the outer layer is substantially straight or straight such that the outer layer, following its manufacture and removal from the second mould, is substantially straight or straight, respectively.

21. A method of forming an implantable electrode array of claim 20 wherein once the carrier is cured, the carrier is removed from the first mould and straightened in a straightening jig.

22. A method of forming an implantable electrode array of claim 21 wherein once the outer layer is cured, the outer layer is removed from the second mould and adhered to the carrier being held in the straightening jig.

23. A method of forming an implantable electrode array of claim 22 wherein once the outer layer is adhered to the carrier, the electrode array formed by this process is removed from the jig and packaged.

* * * * *